US010888842B2

(12) United States Patent
Yoo et al.

(10) Patent No.: US 10,888,842 B2
(45) Date of Patent: Jan. 12, 2021

(54) SOLID CATALYST FOR MANUFACTURING FATTY ACID METHYL OR ETHYL ESTER AND METHOD FOR MANUFACTURING FATTY ACID METHYL OR ETHYL ESTER USING THE SAME

(71) Applicant: Seong Min Yoo, Gwacheon-si (KR)

(72) Inventors: Seong Min Yoo, Gwacheon-si (KR); Jeong Woo Yoo, Anyang-si (KR)

(73) Assignee: Seong Min Yoo, Gwacheon-si (KR)

( * ) Notice: Subject to any disclaimer, the term of this patent is extended or adjusted under 35 U.S.C. 154(b) by 154 days.

(21) Appl. No.: 16/305,536

(22) PCT Filed: Jun. 1, 2017

(86) PCT No.: PCT/KR2017/005734
§ 371 (c)(1),
(2) Date: Nov. 29, 2018

(87) PCT Pub. No.: WO2017/209535
PCT Pub. Date: Dec. 7, 2017

(65) Prior Publication Data
US 2020/0238257 A1    Jul. 30, 2020

(30) Foreign Application Priority Data
Jun. 2, 2016 (KR) .................. 10-2016-0068826

(51) Int. Cl.
B01J 23/34      (2006.01)
B01J 27/02      (2006.01)
B01J 35/02      (2006.01)
B01J 37/00      (2006.01)
B01J 37/04      (2006.01)
B01J 37/08      (2006.01)
C07C 67/08      (2006.01)

(52) U.S. Cl.
CPC ............... *B01J 23/34* (2013.01); *B01J 27/02* (2013.01); *B01J 35/023* (2013.01); *B01J 37/0009* (2013.01); *B01J 37/04* (2013.01); *B01J 37/082* (2013.01); *C07C 67/08* (2013.01)

(58) Field of Classification Search
CPC ... B01J 23/34; B01J 35/08; B01J 27/02; B01J 32/00; B01J 35/023; B01J 37/0009; B01J 37/04; B01J 37/082; B01J 35/02; B01J 35/026; B01J 37/00; B01J 37/0018; B01J 37/02; B01J 37/0201; C07C 67/08; C07C 67/62; C07C 69/003
See application file for complete search history.

(56) References Cited

U.S. PATENT DOCUMENTS

| 4,668,439 A | 5/1987 | Billenstein et al. |
| 5,908,946 A | 6/1999 | Stern et al. |
| 6,037,286 A | 3/2000 | Weiser et al. |
| 2010/0286420 A1 | 11/2010 | Akatsuka et al. |
| 2011/0269621 A1 | 11/2011 | Emori et al. |
| 2012/0130101 A1* | 5/2012 | Yoo .......................... B01J 23/22 554/167 |
| 2015/0018572 A1 | 1/2015 | Oh |

FOREIGN PATENT DOCUMENTS

| EP | 0198243 A2 | 10/1986 |
| EP | 1468734 A1 | 10/2004 |
| GB | 795573 A | 5/1958 |
| JP | 4997681 B2 | 8/2012 |
| JP | 2013-072071 A | 4/2013 |
| KR | 10-2002-0028120 A | 4/2002 |
| KR | 10-0644246 B1 | 11/2006 |
| KR | 10-2010-0056129 A | 5/2010 |
| KR | 2010-0056129 * | 5/2010 |
| WO | 2007012097 A1 | 2/2007 |

OTHER PUBLICATIONS

Verhelst et al. (Catalytic self-cleaning coatings for thermal oxidation of organic deposits on glass Catal. Sci. Technol. 3, pp. 1579-1590, Published 2013) (Year: 2013).*
Shin, Yong-Sub, "Esterification Reaction of Soybean Oil by Heterogeneous Catalysts," J. Life Sci, 2004, v.14 (2), pp. 269-274.
Verhelst, J. et al., "Catlytic Self-cleaning Coatings for Thermal Oxidation of Organic Deposits on Glass," Cat. Sci. & Tech., 2013, vol. 3 (6), pp. 1579-1590.

* cited by examiner

*Primary Examiner* — Clinton A Brooks
*Assistant Examiner* — Blaine G Doletski
(74) *Attorney, Agent, or Firm* — Don D. Cha; HDC IP Law, LLP

(57) ABSTRACT

The present invention relates to a method for manufacturing a catalyst for synthesizing a fatty acid methyl or ethyl ester and a method for manufacturing a fatty acid methyl or ethyl ester using the catalyst. It provides a method for manufacturing a solid catalyst by mixing the oxides of manganese as active catalytic material and the soda lime glass as carrier wherein the content of the oxides of manganese is in the range of 0.1 w % to 70 w %, molding the mixture to spherical or cylindrical shape and sintering the molded catalyst. It also provides a method for manufacturing fatty acid methyl or ethyl ester with high purity by reacting fatty acid or a mixture of oil and fatty acid with methanol or ethanol by placing the solid catalyst in the reactor.

10 Claims, 2 Drawing Sheets

SOLID CATALYST FOR MANUFACTURING FATTY ACID METHYL OR ETHYL ESTER AND METHOD FOR MANUFACTURING FATTY ACID METHYL OR ETHYL ESTER USING THE SAME

CROSS-REFERENCE TO RELATED APPLICATIONS

This application is a 371 U.S. national stage application of PCT patent application No. PCT/KR2017/005734, filed Jun. 1, 2017, which claims the priority benefit of Korean Patent Application No. 10-2016-0068826, filed Jun. 2, 2016, all of which are incorporated herein by reference in their entirety.

FIELD OF THE INVENTION

This invention concerns a solid catalyst for manufacturing fatty acid methyl or ethyl ester, and the method for manufacturing fatty acid methyl or ethyl ester with high purity. This invention treats particularly the simultaneous conversion of oil and fatty acid in the oils containing lots of fatty acid into fatty acid methyl or ethyl ester.

BACKGROUND OF THE INVENTION

The most common catalyst used to synthesis fatty acid methyl or ethyl ester from oil is the soluble strong base catalyst. In general, the soluble strong base catalyst used in the above reaction includes sodium methoxide (MeONa), sodium hydroxide (NaOH), potassium hydroxide (KOH), sodium carbonate (Na2CO3)n and the like. As disclosed in U.S. Pat. No. 4,363,590 Sodium (Na), which is an alkali metal, may be used.

Synthesis of fatty acid methyl or ethyl ester using such a strong base homogeneous catalyst can be easily achieved even at 70° C. or less. However, the homogeneous strong base catalyst reacts with the oil to produce fatty acid soap. In particular, when fatty acids are mixed in the oil, a strong neutralization reaction occurs between the fatty acid and the homogeneous strong base catalyst, consuming the catalyst and producing a large amount of soap. Therefore, when a large amount of fatty acid is present in the reactant, the reactant containing the soap after the reaction forms an emulsion having a high viscosity, making it difficult to purify the fatty acid methyl or ethyl ester. Therefore, in order to produce pure fatty acid methyl or ethyl ester using a strong base homogeneous catalyst, it is necessary to remove soap and catalyst, which requires a lot of complicated processes, which not only greatly increases the manufacturing cost but also causes environmental pollution problems with waste water and waste oil.

In order to convert oils containing lots of fatty acid to a fatty acid methyl or ethyl ester, a strong acid catalyst, such as sulfuric acid or phosphoric acid, is used to react the fatty acid with methanol or ethanol several times in succession to consume fatty acids. And then a solution of a strong base catalyst is added to convert the remaining oil to a fatty acid methyl or ethyl ester. This method is so complex and dangerous that it is very limited in its use.

Accordingly, in order to solve the fundamental problems of the production process of the fatty acid methyl or ethyl ester by using the soluble homogeneous catalyst, the process using the heterogeneous catalyst has been actively studied.

Korean Patent Publication No. 2002-0028120 and Journal of Life Science, Vol. 2. 269 274 (2004) show that ZnO, MgO, CaO, MnO, TiO2 and the like are widely used as powdery heterogeneous catalysts in the production of fatty acid alkyl esters.

European Patent Publication No. 0 198 243 discloses a method for producing fatty acid methyl esters in a fixed bed reactor packed with alumina (Al2O3) or a mixed catalyst of alumina and iron oxide (FeO) and English Patent No. 795 573 discloses a process for producing fatty acid methyl esters by reacting zinc silicate with methanol at 250° C. to 280° C. and 100 bar or less.

Many studies have been made on powdery heterogeneous catalysts. However, since the catalysts are suspended and discharged after the reaction as a mixture form with reactants, they are not advantageous compared with the homogeneous catalysts. Instead, the filters, pumps, valves, the reactors, etc. are blocked, and the production is stopped. Practical application is not possible since the risk of accidents is so high.

In addition, the active catalytic metal component of the powdery heterogeneous catalyst easily reacts with a fatty acid to form a metal soap, which is discharged to cause serious problems in refining the product. It also confirmed that the metal soap leached out in the above process can catalyze the synthesis of fatty acid alkyl ester. U.S. Pat. No. 4,668,439 discloses a method of using a metal soap such as zinc laurate as a catalyst at 210° C. to 280° C. and normal pressure. International Patent Publication No. WO 2007/012097 shows a method to synthesis fatty acid alkyl ester using a liquid metal catalyst which is an alkaline earth metal salt of carboxylic acid like a metal soap such as magnesium stearate.

There is a great need to develop a catalyst in which the catalyst remains in the reactor without being discharged to continuously serve as a solid catalyst. European Patent Laid-Open Publication No. 1 468 734 shows a method of obtaining a catalyst of ZnAl2O4.xZnO.yAl2O3. This patent discloses a method of doping zinc oxide (ZnO), which is an active material, on a carrier. In detail, water and nitric acid, which are strong acids, are physically mixed with an alumina gel containing 25% of water and then nitric acid compounds such as zinc oxide (ZnO), zinc carbonate (ZnCO3) and zinc nitrate (ZnNO3) are mixed and liquified. After liquefaction, zinc ions are adhered to the surface of the alumina gel and sintered at a temperature of 1000° C. or lower to prepare a catalyst having a spinel structure. On the other hand, there is a high risk when using a strong acid in the production of a catalyst and corrosion and pollution can occur.

Although the structure of the catalyst is similar to that of the above catalyst, a method for producing a fatty acid alkyl ester using a heterogeneous catalyst prepared by another production method is disclosed in U.S. Pat. No. 5,908,946. It discloses the production process of fatty acid alkyl ester and high purity glycerin using a catalyst with a spinel structure of ZnAl2O4.xZnO.yAl2O3 (x,y=0~2) in discontinuous process or continuous process made of a fixed bed reactor or many autoclaves in parallel. According to this, powder, pellet and ball types of ZnAl2O4.xZnO.yAl2O3 catalyst with a spinel structure containing zinc oxide are used for the reaction of vegetable and animal oil with alcohol at 170° C. to 250° C. and 100 bars. These reactions produced fatty acid alkyl ester with a purity of 97% maximum and glycerin having a purity of 99.5% or more. It also shows that the fatty acid alkyl ester is purified by distillation to get a purity of 99.8% or more. Here, the catalyst to be treated as main inventions includes (1) a method in which a zinc salt is dissolved in water to be doped on an alumina ball, followed by drying and sintering; (2) various methods using the zinc compounds such as zinc oxide, zinc hydroxide, zinc carbonate and zinc hydroxy carbonate etc. (3) a method for producing a catalyst by coprecipitating zinc salts dissolved in water and aluminum salts (aluminum nitrate, aluminum sulfate, aluminum acetate, etc.) dissolved in water, and the like. In the method (3), the dissolved salt is coprecipitated with a hydrotalcite structure after appropriately adjusting the pH with sodium carbonate, sodium aluminate, sodium bicarbonate, etc., and then sodium is removed by washing. After dehydration, the catalyst having a spinel structure is prepared with heat treatment at 400° C. However, when a catalyst is prepared by using such a method, the use of strong acids such as nitric acid, sulfuric acid, and acetic acid necessitates a neutralization process, and a large amount of waste water is generated in this process. Further, when a catalyst containing a small amount of nitric acid, sulfuric acid, and acetic acid is sintered, air pollutants such as nitrogen oxides (NOx) and sulfur oxides (SO) are generated.

As a similar patent, Korean Patent Publication No. 10-0644246 discloses a continuous process which consists of several reactors to produce fatty acid alkyl ester and high purity glycerin using a catalyst having a spinel structure of xMgO.yZnO.ZnAl2O4 (x=1 to 3, y=0 to 2). It is only difference to use zinc salt as well as magnesium salt (nitrogen, chlorine, acetate) as the catalytic materials compared with the method (3) of the above-mentioned U.S. Pat. No. 5,908,946 in which zinc salt is used alone as the catalytic material. An aqueous solution of an alkaline precipitant (sodium hydroxide, sodium carbonate, sodium bicarbonate) is added to an aqueous solution where magnesium, aluminum and zinc salts (nitrogen, chlorine, acetate) are dissolved to form hydroxide precipitates, which are separated, washed, dried and sintered to be the catalyst with a spinel structure.

The method of adhering active metal oxides using nitric acid to an alumina carrier has limitations on the use of the invented technique in addition to the pollution problem. The active metal oxide that is insoluble in nitric acid is difficult to be doped on the carrier because it cannot be hydrated, making it impossible to utilize the above method. On the other hand, the metal component doped on the carrier in the ionic state reacts with the fatty acid in the reactant to make metal soap, and the active material such as zinc easily leaches and the catalyst loses its function.

Korean Patent Publication No. 10-2010-0056129 proposes a new method for solving such a problem. Active catalytic materials composed of at least one of oxides, carbonates and hydroxides of magnesium, calcium, zinc, titanium, manganese, vanadium, beryllium, copper, zirconium, strontium, tin and barium (for example, MgO, Mg(OH)2, MgCO3, etc.) are mixed with clay of the silica alumina type (AlxSiyOzMn(H2O)m) and sintered at a high temperature of 1000° C. to 1500° C. to produce a ceramic metal catalyst having porosity. This ceramic catalyst showed no pollution during the production and showed that it is possible to effectively convert oil to fatty acid alkyl esters.

However, clay of the silica alumina type has to be mixed with active catalytic materials to make dough, which has so high viscosity that it is difficult to mold a catalyst. Moreover, it has to be sintered at a high temperature of 1000° C. or more, the activity of active catalytic material can be much decreased. And in the case of using a raw material containing a large amount of fatty acid, the fatty acid reacts with the active catalytic material of the catalyst to produce metal soap, and the leaching of the active catalytic material can not be avoided.

In summary, the conventional catalysts are problematic in that (1) when a soluble homogeneous catalyst is used, a large amount of soap is generated and the purification process is very difficult, (2) when a metal oxide powder catalyst is used, the powder is mixed with reactants making it impossible to produce continuously, (3) when using a solid catalyst prepared by solution doping method, it is difficult to use a strong acid in the production of the catalyst, and when the fatty acid is present in the reactant, the catalyst is leached and the activity is decreased, and (4) when the ceramic solid catalyst using clay is used, sintering at a high temperature may cause problems such as abrupt decrease of the activity of the catalyst and leaching of the active catalytic materials.

SUMMARY OF THE INVENTION

The present invention has been made to solve the above problems, and it is an object of the present invention to provide a solid catalyst capable of efficiently producing fatty acid methyl or ethyl ester over a long period of time by maintaining the activity of the solid catalyst and preventing leaching.

It is also an object of the present invention to provide a solid catalyst which can be produced in the form of a solid, such as a cylindrical or spherical shape, having a high strength of the solid catalyst, and can maintain a solid state during the production of fatty acid methyl or ethyl ester.

It is also an object of the present invention to provide a solid catalyst which is physically and chemically stable so that the leaching of the catalyst by the fatty acid is minimized even when a raw material containing a large amount of fatty acid is used.

It is also an object of the present invention to provide a method for manufacturing a solid catalyst in a simple and economical manner.

It is also an object of the present invention to provide a method for converting oils containing lots of fatty acid into a fatty acid methyl ester or ethyl ester using the solid catalyst.

In order to achieve the above object, the present invention provides the method of preparing solid mixture of carrier and active catalytic materials which consists of an oxide of manganese powder, or of a combination of two or more as cylindrical or spherical forms that can be filled in a fixed bed reactor for manufacturing fatty acid methyl or ethyl ester. Though the manganese powder itself has good catalytic activity to produce fatty acid methyl or ethyl ester, it cannot be filled in packed-bed column reactor because of its powdery form. It heavily interrupts production process by blocking control valve, pump, filter etc. and also requires complicated separation processes to remove the metal catalyst after reaction.

The oxide of manganese exists in a wide variety of oxides such as MnO, MnO2, Mn2O3, Mn3O4, and the like. In addition, MnO2 also presents as a typical polymorphism material as α-MnO2, β-MnO2. On the other hand, manganese oxide is very sensitive to heat and when it is heated, MnO2 is converted into Mn2O3 at 700° C., and Mn2O3 is converted into Mn3O4 at 950° C. under air.

Although the oxide of manganese in powder form can be a useful catalyst in synthesizing fatty acid methyl or ethyl ester from the oils, it is very difficult to make a solid catalyst by doping it on a carrier. As a result, the process using the catalyst has not been commercialized for the past several decades.

In order to dope the powder of the oxide of manganese on a carrier, it should be done at lower than temperature at which the activity is maintained. Therefore, theoretically, it requires difficult and hazardous process like followings; MnO2 is reacted with N2O4 to form Mn (NO3)2, or MnO is formed by carbothermal reduction method. Either of them is dissolved in sulfuric acid, and the carrier is immersed in these strong acid aqueous solutions, and ammonium carbonate is added to get MnCO3, which is doped on the carrier. The MnCO3 doped carrier is treated by heat.

On the other hand, it is more difficult to immobilize the powdered oxide of manganese to the carrier thermally. According to the aforementioned Korean Patent Laid-Open No. 10-2010-0056129, temperature of at least 1000° C. is required to mix and immobilize the powdered oxide of manganese with the silica alumina clay. For this reason, the claims of the above patent are also limited to the clay-supported catalyst sintered at 1000° C. or higher. Oxide of manganese, however, causes a significant change in the catalytic activity to convert oil and fatty acid to fatty acid methyl or ethyl ester from 800° C., and when the temperature exceeds 950° C., the catalytic activity is completely lost. In the above patent, the catalyst obtained by mixing MnO and clay and sintering at 1250° C. has good moldability, but the fact that the reaction result is not shown as an example using this catalyst means that it does not act as a catalyst.

The present invention provides a solid catalyst with high compressive strength and porosity while maintaining a predetermined shape consistently before and after the reaction by thermally sintering powdered oxide of manganese and soda lime glass as a carrier material together while maintaining the activity of the catalyst.

Oils containing lots of fatty acid cannot be used for manufacturing fatty acid methyl or ethyl ester by the soluble strong base catalyst, which is saponified by the fatty acid. The present invention solves the problem achieving the effect of producing fatty acid methyl or ethyl ester at a competitive price by using those low-cost oils as raw materials. In addition, since the saponified product is fundamentally prevented from being produced after the reaction, a complex process of purifying and separating the saponified catalyst from the product is not required.

In contrast to conventional solid catalysts in the form of powders, the solid catalysts by the present invention can maintain the predetermined shape before and after the reaction because it is not a powder type but a catalyst doped on porous carrier with high compressive strength. It also can solve the problem that when the powdery solid catalyst is used, it is difficult to remove it from the reaction product.

In addition, the present invention to manufacture the catalyst at 950° C. and less can solve the problem of loss of catalytic activity of a ceramic carrier of silica alumina clay which has to be prepared at 1000° C.

In conclusion, the present invention provides the cylindrical or spherical shaped solid catalyst with strength and porosity for transesterification or esterification to produce fatty acid methyl or ethyl ester by sintering a soda lime glass as a carrier and oxide of manganese which has good catalytic material but cannot be shaped cylindrically or spherically with enough strength by itself.

Typical commercial soda lime glass consists of SiO2 as the main component and the mixture of $Na_2O$, CaO, Al2O3, K2O, SO3, MgO, Fe2O3, and TiO2, which are impurities. The composition, it is slightly different by samples, is SiO2 (73-76 wt %), $Na_2O$ (12-15 wt %), CaO (8-11 wt %), Al2O3 (0-2 wt %), K2O (0-1 wt %), SO3 (0-0.5 wt %), MgO (0-0.5 wt %), Fe2O3 (0-1 wt %) and TiO2 (0-0.5 wt %). Because each component is completely melted and distributed, it has no inherent property and only shows an inert glass property.

Soda lime glass, like oxide of manganese, is a typical polymorphic material composed of a mixture of amorphous materials that are somewhat different in shape depending on the type of impurities. Soda lime glass has a melting point of about 1000° C. and a glass transition temperature of about 570° C., while pure silicon oxide (SiO2) has a high crystallinity and has a melting point of 1723° C. By the inclusion of impurities, the physicochemical properties of the material are changing significantly.

When the soda lime glass is above the glass transition temperature, the diffusion of each component becomes possible, and the powder soda lime glass molded into a specific shape such as a cylindrical shape causes surface diffusion at the contacted micro-surfaces and gradually sticks to each other. It makes a porous form with high hardness.

When the soda lime glass powder and the oxide of manganese, the adhesion aid, and the lubricating aid are mixed and molded through compression in a cylindrical or circular mold and then sintered at an optimum temperature for a predetermined time, the adhesion aid and the lubricating aid are carbonized and removed. After that, the oxide of manganese begins to diffuse slowly from the soda lime glass surface and slowly dopes. The oxide of manganese oxide is doped at a safe temperature to preserve the catalytic activity, and when the molecular diffusion bonding is completed even between the soda lime glass powders, it is converted into a solid catalyst having high hardness while the catalytic activity is maintained.

The catalyst doped on the soda lime glass can give the advantageous effect of the solid catalyst if it maintains sufficient strength to impact by the stirring in stirred tank reactor and withstands impact by the weight of the catalyst in fixed bed reactor. Accordingly, in order to allow the solid catalyst to maintain its own shape before and after the reaction, the active catalytic material of the solid catalyst is preferably limited to an amount of 0.1 wt % to 70 wt % of the catalyst doped on the soda lime glass.

In the present invention, a method for manufacturing a solid catalyst having a certain shape will be described in detail.

The carrier material soda lime glass powder and the active catalytic material are mixed in a ratio of 99.9:0.1~30:70, and then an adhesion aid, a lubricating aid, and a porosity enhancer are added, mixed and then dried. The mixed catalyst powder is compression molded into a cylindrical or spherical shape and sintered at a temperature higher than the glass transition temperature of 570 to 950° C., preferably 650 to 800° C. for 10 to 120 minutes. The catalyst doped on the soda lime glass is made according to this invention.

The catalyst doped on the soda lime glass according to the present invention is much different not only in the structural characteristics but also in the manufacturing method compared to the catalyst xMgO.yZnO.ZnAl2O4 having the spinel structure disclosed in Korean Patent Publication No. 10-0644246 and the catalyst ZnAl2O4.xZnO.yAl2O3 having the spinel structure disclosed in U.S. Pat. No. 5,908,946. In other words, when a material such as Al2O3 disclosed in Korean Patent Publication No. 10-0644246 or U.S. Pat. No. 5,908,946 is sintered at 1000° C. or less, a catalyst with hardness cannot be achievable. Instead, a new compounds are prepared using a metal salt under strong acid and then they are converted to the catalysts having a spinel structure by calcination at a temperature of not more than 1000° C.

In addition, compared with of Korean Patent Laid-Open Publication No. 10-2010-0056129, the catalyst doped on the soda lime glass according to the present invention is not only different from the carrier structure of silica alumina (AlxSiyOzMn(H2O)m) but also different from the preparation condition in which active catalytic material and clay as a carrier are mixed with water and then the mixture is sintered at 1000° C. or higher.

The present invention provides the method for manufacturing fatty acid methyl or ethyl ester by reacting oil containing fatty acid with methanol or ethanol by equivalent ratio of 1:1 to 1:10 in the solid catalyst packed reactor maintaining the temperature at 170-250° C. and pressure at 10-60 bar.

The reaction is carried out in a batch reactor and a continuous fixed bed reactor.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF THE INVENTION

Figure 1:
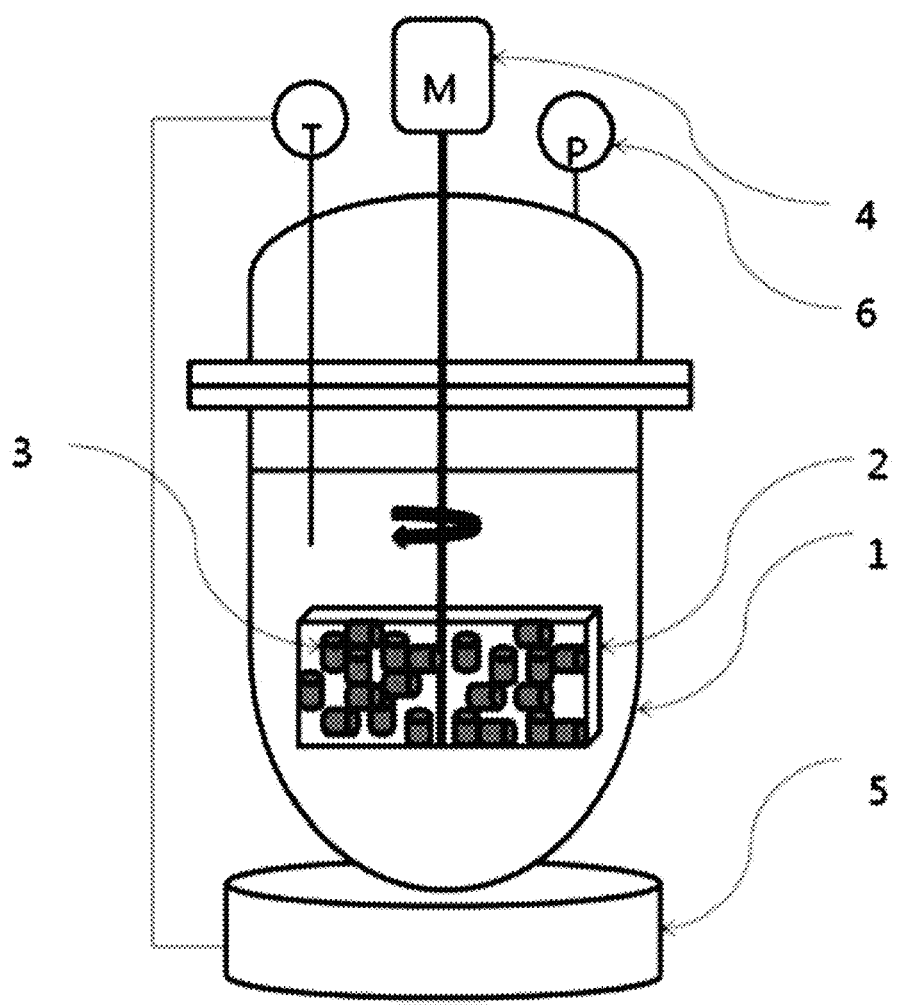
FIG. 1 is the schematic diagram of a non-continuous reactor for manufacturing fatty acid methyl or ethyl ester according to the present invention.

Hereinafter, examples of the present invention will be described in detail.

In describing the present invention, a detailed description of well-known functions or constructions will be omitted for clarity of the present invention. In addition, even if the kind of the at least one minor amount of the soda lime glass is changed or the content thereof is slightly different, the catalytic action and the physical properties such as the compressive strength of the solid catalyst finally produced are hardly affected. In order to clarify the structure and operation effects of the soda lime glass according to the present invention, the metal oxide components constituting the soda lime glass will not be listed in the examples of the present invention.

First, a method for manufacturing a ceramic metal catalyst according to the present invention will be described in detail.

Example 1: Preparation of a Solid Catalyst for the Synthesis of Fatty Acid Methyl or Ethyl Ester from Oil Containing Fatty Acid Solid catalysts are prepared by varying the ratio of the carrier material, soda lime glass, and manganese dioxide, which is an active catalytic material. As shown in Table 1, the mixing ratio of the carrier material and the active catalytic material was varied, and a small amount of the adhesion aid, the lubricating aid, and the porosity enhancer were uniformly mixed.

A cylindrical mold having a diameter of 8 mm and a length of 12 mm is filled with a catalyst mixture and molded into a cylindrical shape under pressure. Cylindrical catalysts were sintered at 750° C. for 40 minutes to prepare solid catalysts. The results were as follows.

TABLE 1

| Example | Carrier | Catalyst material | Diameter of the catalyst | Compressive strength |
|---|---|---|---|---|
| 1-1 | Soda lime glass 90 g | MnO$_2$ 10 g | 8 mm | 115 kg/cm2 |
| 1-2 | Soda lime glass 60 g | MnO$_2$ 40 g | 8 mm | 83 kg/cm2 |
| 1-3 | Soda lime glass 30 g | MnO$_2$ 70 g | 8 mm | 39 kg/cm2 |

As shown in Table 1, when the weight ratio of the active catalytic material is increased, the reaction yield shown in Table 4 is high. However, the solid catalyst having 70 wt % of the active material has a remarkably low compressive strength and is expected to be broken. The active catalytic material is thus controlled not to exceed 70 wt % of the solid catalyst.

Example 2: Preparation of a Solid Catalyst for the Synthesis of Fatty Acid Methyl or Ethyl Ester from Oil Containing Fatty Acid Solid catalysts were prepared by sintering the molded catalyst composed of 60 wt % of soda lime glass as a carrier material and 40 wt % of manganese dioxide as an active catalytic material at different temperatures. As shown in Table 2, the mixing weight ratio of the carrier material and the active catalytic material was uniformly mixed, and a small amount of the adhesion aid and the lubricating aid, and the porosity enhancer were uniformly mixed.

A cylindrical mold having a diameter of 8 mm and a length of 12 mm is filled with a catalyst mixture and molded into a cylindrical shape under pressure. The catalysts prepared in cylindrical form were sintered at 550° C.-950° C. for 40 min to prepare solid catalysts. The results were as follows.

TABLE 2

| 2-1 | Soda lime glass 60 g | MnO$_2$ 40 g | 8 mm | 550° C. | 6 kg/cm2 |
| 2-2 | Soda lime glass 60 g | MnO$_2$ 40 g | 8 mm | 650° C. | 63 kg/cm2 |
| 2-3 | Soda lime glass 60 g | MnO$_2$ 40 g | 8 mm | 750° C. | 90 kg/cm2 |
| 2-4 | Soda lime glass 60 g | MnO$_2$ 40 g | 8 mm | 850° C. | 127 kg/cm2 |
| 2-5 | Soda lime glass 60 g | MnO$_2$ 40 g | 8 mm | 950° C. | 162 kg/cm2 |

As can be seen from Table 2, when the sintering temperature was 550° C., a catalyst having a very low hardness was obtained and was not suitable for use. From 650° C., solid catalysts with good hardness were obtained. Solid catalysts which can be used sufficiently for the synthesis of fatty acid methyl ester or ethyl ester were obtained.

Example 3: Preparation of a Solid Catalyst for the Synthesis of Fatty Acid Methyl or Ethyl Ester from Oil Containing Fatty Acid Solid catalysts were prepared by sintering the molded catalyst composed of 60 wt % of soda lime glass as a carrier material and 40 wt % of manganese dioxide as an active catalyst material at 750° C. for various sintering time. As shown in Table 3, the mixing weight ratio of the carrier material and the active catalytic material was uniformly mixed, and a small amount of the adhesion aid and the lubricating aid, and the porosity enhancer were uniformly mixed.

A cylindrical mold having a diameter of 8 mm and a length of 12 mm is filled with a catalyst mixture and molded into a cylindrical shape under pressure. Cylindrical catalysts were sintered at 750° C. for 10~120 minutes to produce solid catalysts.

TABLE 3

| | | | | |
|---|---|---|---|---|
| 3-1 Soda lime glass 60 g MnO$_2$ 40 g | 8 mm | 10 min | 23 kg/cm2 |
| 3-2 Soda lime glass 60 g MnO$_2$ 40 g | 8 mm | 20 min | 63 kg/cm2 |
| 3-3 Soda lime glass 60 g MnO$_2$ 40 g | 8 mm | 30 min | 84 kg/cm2 |
| 3-4 Soda lime glass 60 g MnO$_2$ 40 g | 8 mm | 40 min | 92 kg/cm2 |
| 3-5 Soda lime glass 60 g MnO$_2$ 40 g | 8 mm | 60 min | 102 kg/cm2 |
| 3-6 Soda lime glass 60 g MnO$_2$ 40 g | 8 mm | 120 min | 107 kg/cm2 |

As can be seen from Table 3, it was confirmed that the sintering time of 10 minutes was somewhat insufficient at 750° C. After a sintering time of 20 minutes, Solid catalysts with good strength were obtained. They can be used sufficiently for the synthesis of fatty acid methyl or ethyl ester.

Example 4: Synthesis of a Fatty Acid Methyl Ester from Oil Containing Fatty Acid A fatty acid methyl ester was synthesized by adding oil containing fatty acid and methanol using the capped reactor (1) having a capacity of 250 ml shown in FIG. 1. A porous box (2) which can be filled with catalyst is installed on the shaft of the stirrer provided at the center of the reactor, and the solid catalyst (3) is filled therein, and then rotated by the motor (4). At the start of the reaction, the cab of the reactor was opened first, and 20 g of the solid catalyst prepared in Example 1, Example 2 and Example 3 was exchanged and installed in the porous box (2) each time the reaction was carried out. 100 g of the waste cooking oil containing 30% of fatty acid and 30 g of methanol are filled, the lid is closed, and the motor (4) is rotated to mix the reactants. The temperature inside the reactor is heated to 200° C. by a temperature controller (5) to control the temperature inside. When the internal temperature reached 200° C., the reaction was continued at the same temperature for 2 hours. It was confirmed that the reaction pressure was 24-32 bars by the pressure gauge (6). After the completion of the reaction, the reactor is cooled by passing the cooling water through the temperature controller and the cap is opened to take the sample from hydrophobic phase and the methanol component was removed from the sample. The concentration of the fatty acid methyl ester in the reaction product is analyzed by gas chromatography to calculate the product purity and the acid value was measured by acid-base titration. The results are as follows.

TABLE 4

| Example | Catalyst used | Content of fatty acid methyl ester (wt %) | Acid value |
|---|---|---|---|
| 4-1 | Example 1, 1-1 catalyst | 83.5 | 9.6 |
| 4-2 | Example 1, 1-2 catalyst | 91.9 | 7.2 |
| 4-3 | Example 1, 1-3 catalyst | 93.3 | 6.5 |
| 4-4 | Example 2, 2-2 catalyst | 92.8 | 5.8 |
| 4-5 | Example 2, 2-3 catalyst | 93.1 | 6.1 |
| 4-6 | Example 2, 2-4 catalyst | 82.6 | 7.4 |
| 4-7 | Example 2, 2-5 catalyst | 65.9 | 9.9 |
| 4-8 | Example 3, 3-1 catalyst | 92.2 | 5.3 |
| 4-9 | Example 3, 3-2 catalyst | 93.4 | 5.1 |
| 4-10 | Example 3, 3-3 catalyst | 91.8 | 6.7 |
| 4-11 | Example 3, 3-4 catalyst | 93.5 | 6.3 |
| 4-12 | Example 3, 3-5 catalyst | 90.4 | 6.4 |
| 4-13 | Example 3, 3-6 catalyst | 90.1 | 7.1 |

Table 4 shows the results of carrying out the reaction using the solid catalysts prepared in Examples 1 to 3. Fatty acid methyl esters with high purity of 90% or more were able to be produced even when the methanol content was 30% of oil. However, it was confirmed that when the active catalytic material is used in a small amount of 10% and when the sintering temperature of the solid catalyst is more than 850° C., the yield is drastically reduced.

On the other hand, an advantage that the process is simplified can be obtained since the used solid catalyst is fixed in the solid state without breakage in the reactor, the catalyst is not contained in the fatty acid methyl ester after the reaction and thus the step of separating the catalyst from the reaction product is not necessary.

Example 5: Synthesis of a Fatty Acid Ethyl Ester from Oil Containing Fatty Acid

A fatty acid ethyl ester was synthesized by adding oil containing fatty acid and ethanol using the capped reactor (1) having a capacity of 250 ml shown in FIG. 1. A porous box (2) which can be filled with catalyst is installed on the shaft of the stirrer provided at the center of the reactor, and the solid catalyst (3) is filled therein, and then rotated by the motor (4). At the start of the reaction, the cap of the reactor was opened first, and 20 g of the solid catalyst prepared in Example 1 was installed in the porous box (2) to carry out the reaction. 100 g of the waste cooking oil containing 30% of fatty acid and 40 g of anhydrous ethanol are filled, the lid is closed, and the motor (4) is rotated to mix the reactants. The temperature inside the reactor is heated to 200° C. by a temperature controller (5) to control the temperature inside. When the internal temperature reached 200° C., the reaction was continued at the same temperature for 2 hours. It was confirmed that the reaction pressure was 25 bars by the pressure gauge (6). After the completion of the reaction, the reactor is cooled by passing the cooling water through the temperature controller and the cap is opened to take the sample from hydrophobic phase and the ethanol component was removed from the sample. The concentration of the fatty acid ethyl ester in the reaction product is analyzed by gas chromatography to calculate the product purity and the acid value was measured by acid-base titration. The results are as follows.

TABLE 5

| Example | Catalyst used | Content of fatty acid methyl ester (wt %) | Acid value |
|---|---|---|---|
| 5-1 | Example 1, 1-2 catalyst | 92.3 | 6.8 |

Table 5 shows that when the reaction was carried out using the 1-2 solid catalyst prepared in Example 1, fatty acid ethyl ester with high purity of 92.3% was able to be produced when the ethanol content was 40% of oil.

Figure 2:
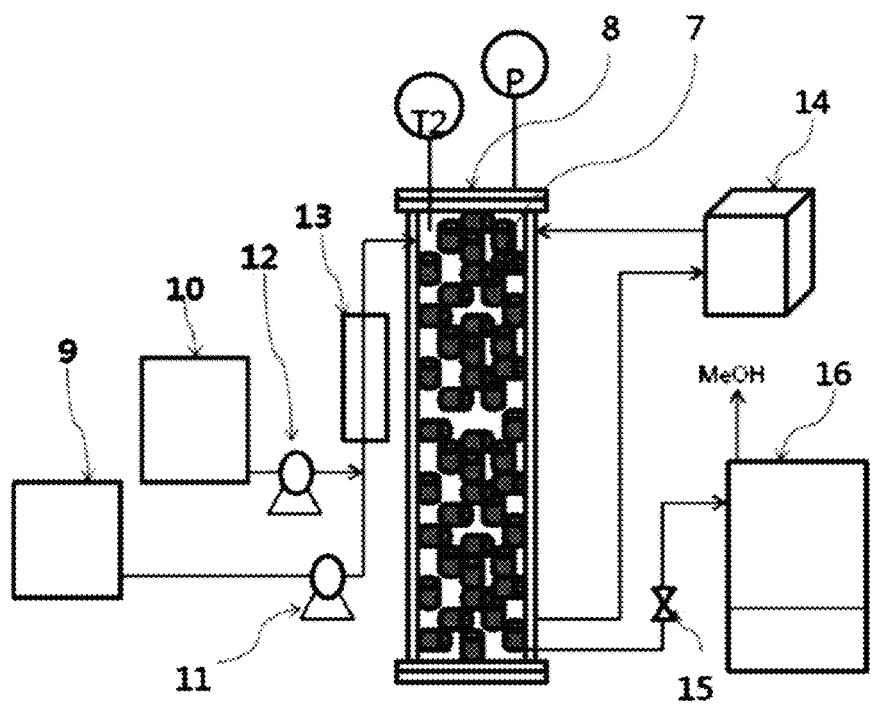
FIG. 2 is the schematic diagram of a continuous fixed bed reactor for manufacturing fatty acid methyl or ethyl ester according to the present invention.

Example 5: Synthesis of a Fatty Acid Methyl Ester from Oil Containing Fatty Acid Fatty acid methyl ester was synthesized by adding oil containing fatty acid and methanol using the continuous fixed bed reactor shown in FIG. 2.

Figure 3:
FIG. 3 is the chemical reaction showing esterification to manufacture fatty acid methyl or ethyl ester according to the present invention.
Figure 4:
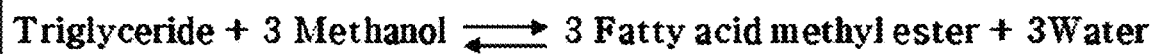
FIG. 4 is the chemical reaction showing transesterification to manufacture fatty acid methyl or ethyl ester according to the present invention.

350 kg of the 1-2 catalyst (7) of Example 1 is filled in the continuous fixed-bed reactor having an inner capacity of 300 liters (8) and the lid is closed. Palm oil containing 30% of fatty acid is prepared in the raw material oil container (9) having a capacity of 2,000 liters equipped with a stirrer, and methanol is prepared in the methanol container having a capacity of 500 liters (10). Palm oil containing fatty acid and methanol are supplied at the speed of 100 kg per hour by the metering pump (11) and 15-30 kg per hour by the metering pump (12), respectively. The temperature of the reaction mixture is controlled to 200° C. by a heat exchanger (13). Internal temperature of the reactor is maintained by the hot oil boiler system (14). The residence time of the reactants is 1 hour, and the reactants discharged continuously from the reactor are collected in the vessel (16) collecting the reaction products after passing through the pressure regulating valve (15). The evaporated methanol is sent to the methanol refining process. The direction to inject the reactant into the reactor can be both top and bottom, and when it is injected from the top, the glycerin produced as a byproduct in the reaction is easily discharged. An example of this was proceeded. Particularly, when glycerin and water whose specific gravity are higher than that of fatty acid methyl ester are separated from the hydrophobic component, they are rapidly transported to the lower part of the reactor. Since water and glycerin are removed from the solid catalyst in contact with the lipophilic group because the oil is rapidly transported to the lower part of the reactor, advantage of promoting the forward reaction shown in Reaction 1 and 2 of FIGS. 3 and 4 arises. Therefore, the present invention can increase the fatty acid methyl ester content by lowering methanol content in the reactants.

Methanol was removed from the reaction product, the concentration of the fatty acid methyl ester in the reaction product is analyzed by gas chromatography to calculate the product purity and the acid value was measured by acid-base titration. The results are as follows.

TABLE 6

| Example | Catalyst used | Methanol content to the oil (wt %) | Content of fatty acid methyl ester (wt %) | Acid value |
|---|---|---|---|---|
| 6-1 | Example 1, 1-2 catalyst | 15 | 92.5 | 6.8 |
| 6-2 | Example 1, 1-2 catalyst | 20 | 93.1 | 7.1 |
| 6-3 | Example 1, 1-2 catalyst | 25 | 92.8 | 6.4 |
| 6-4 | Example 1, 1-2 catalyst | 30 | 92.9 | 6.3 |

The solid catalyst of the present invention is very effective for a continuous fixed-bed reactor and shows a very high yield of 90% or more even though the content of methanol is low. Furthermore, even if a low cost raw material containing a large amount of fatty acid is used, no soap or a catalyst component does not contaminate the reaction product, and it is possible to simultaneously secure high value addition of waste, prevention of environmental pollution and high economic efficiency.

According to the above-described present invention, the following effects can be expected.

As described above, the present invention provides the advanced concept solid catalyst which is the soda lime glass on which the oxide of manganese doped. The carrier was mixed with 0.1-70 w % of active catalytic materials composed of at least one oxide of manganese and then sintered together to have very high hardness.

The present invention also provides method of manufacturing high purity fatty acid methyl or ethyl ester with the maximum yield by fixing the solid catalyst inside of the reactor to react oil and fatty acid with methanol or ethanol simultaneously. It does not need the process to remove and refine catalysts.

What is claimed is:

1. A solid catalyst with a non-crystalline porous structure that is adapted for converting oil containing a fatty acid to fatty acid methyl or ethyl ester, wherein said solid catalyst is prepared by (i) mixing an oxide and/or oxides of manganese as active catalytic material and soda lime glass as carrier that consists of SiO2 as the main component and an impurity mixture comprising $Na_2O$, CaO, $Al_2O_3$, $K_2O$, $SO_3$, MgO, $Fe_2O_3$, and $TiO_2$ to obtain a mixture, (ii) molding the mixture, and (iii) sintering the molded mixture to produce said solid catalyst having a non-crystalline porous structure, wherein said solid catalysts comprises:
   73-76 wt % of $SiO_2$,
   12-15 wt % of $Na_2O$,
   8-11 wt % of CaO,
   2 wt % or less of $Al_2O_3$,
   1 wt % or less of $K_2O$,
   0.5 wt % or less of $SO_3$,
   0.5 wt % or less of MgO,
   1 wt % or less of $Fe_2O_3$, and
   0.5 wt % or less of $TiO_2$.

2. The solid catalyst according to claim 1, wherein said the oxides of manganese comprises MnO, MnO2, Mn2O3, Mn3O4, and a mixture thereof.

3. The solid catalyst according to claim 1, wherein the solid catalyst is in a cylindrical shape, or a spherical shape.

4. The solid catalyst according to claim 1, wherein an active catalytic material comprises 0.1 wt % to 70 wt % of the solid catalyst.

5. A process for manufacturing the solid catalyst according to claim 1, said process further comprising the steps of
   (A) Mixing an adhesion aid, a lubricating aid and a porosity enhancer with the mixture to obtain a mixed catalyst powder;
   (B) filling a cylindrical or circular mold with the mixed catalyst powder to produce a molded catalyst through compression of the filled cylindrical or circular mold; and
   (C) Sintering the molded catalyst at a temperature of 550° C. to 950° C. for 10-120 minutes to disperse and stabilize the active catalytic material on the carrier.

6. The process for manufacturing the solid catalyst according to claim 5, wherein the adhesive aid is selected from the group consisting of edible oils, biodiesel, mineral oils, lubricating oils, a porosity enhancer, and a combination thereof.

7. A process for manufacturing fatty acid methyl or ethyl ester by simultaneously reacting an oil comprising a fatty acid with methanol or ethanol, wherein the equivalent ratio of oil comprising the fatty acid to methanol or ethanol is in the range of 1:1 to 1:10, by placing the solid catalyst according to claim 1 and the oil comprising the fatty acid and the methanol or ethanol inside a reactor, maintaining the temperature inside the reactor at 170° C. to 250° C. and the pressure at 10 bars to 60 bars.

8. The process for manufacturing fatty acid methyl or ethyl ester according to claim 7, wherein the solid catalyst according to claim 1 is placed in a continuous fixed bed reactor, reactants are injected into bottom of the reactor and reacted while being moved upward.

9. The process for manufacturing fatty acid methyl or ethyl ester according to claim 7, wherein the solid catalyst according to claim 1 is placed in a continuous fixed bed reactor, reactants are injected into top of the reactor and reacted while being moved downward.

10. The process of claim 6, wherein said porosity enhancer is inert materials selected from the group consisting of cellulose, plastic powder, clay, and a combination thereof.

* * * * *